United States Patent [19]

Cohen et al.

[11] Patent Number: 4,892,813

[45] Date of Patent: Jan. 9, 1990

[54] METHOD FOR THE DETERMINATION OF THE ENZYMATIC ACTIVITY OF CONVERTASE

[75] Inventors: Paul Cohen, Paris; Alain Morel, Puteaux; Sophie Gomez, Issy les Moulineaux; Christine M. Clamagirand; Pablo Gluschankof, both of Paris; Pierre Nicolas, Argenteuil; Hamadi Boussetta, Paris, all of France

[73] Assignee: Centre National de la Recherche Scientifique, Paris, France

[21] Appl. No.: 117,896

[22] Filed: Oct. 30, 1987

Related U.S. Application Data

[63] Continuation of Ser. No. 796,042, Nov. 7, 1985, abandoned.

[51] Int. Cl.[4] .................. C12Q 1/00; C12Q 1/34; C12Q 1/36; C12Q 1/38
[52] U.S. Cl. .................................. 435/4; 435/18; 435/23; 435/24; 435/212; 435/219
[58] Field of Search ............. 435/4, 23, 24, 212, 435/219, 18

[56] References Cited

PUBLICATIONS

Clamagirand et al., Biochem. Biophys. Res. Commun (1986) 134:1190.
Cohen, Biochimie (1987) 69:87–89.
Gluschankof et al., J. Biol. Chem. (1987) 262:1–6.
Gomez et al., "The Somatostatin-28 Convertase of Rat Brain Cortex is Associated with Secretory Granule Membranes." *J. Biol Chem.* vol. 260, No. 19, pp. 10541–10545 (Sep. 5, 1985).
Gluschankof, et al., "The somatostatin-28 Convertase of Rat Brain Cortex Generates Both Somatostatin-14 and Somatostatin-28 (1–12)" *Biochem. and Biophys. Res. Comm.* vol. 128, No. 3, May 16, 1985, pp. 1051–1057.
Gluschankof et al., "Enzymes Processing somatostatin precursors: An Arg-Lys esteropeptidase . . . " *Proc. Natl. Acad Sci* USA, vol. 81, pp. 6662–6666 (Nov. 1984).
Ruggere et al., "Hepatic Metabolism of Somatostatin-14 and Somatostatin-28: Immunochemical Characterization of the Metabolic Fragments and Comparison of Cleavage Sites", *Endocrinolgy* vol. 117, No. 1, pp. 88–96.
Akopian, et al. *Vopr Biokhim Mozsa*, 1978, 13 pp. 189–205 (abstract only).

*Primary Examiner*—Esther M. Kepplinger
*Attorney, Agent, or Firm*—Bertram I. Rowland

[57] ABSTRACT

The invention relates to a method for measuring the enzymatic activity of a convertase, wherein:
(a) a biological sample containing the convertase is brought into contact with a labeled peptide substrate consisting of at least 10 AA, reproducing or mimicking the sequence of the precursor at the excision site, and
(b) after conversion, the enzymatic activity of the sample is measured by determining the percentage of labeled conversion fragments relative to one or more standards.

7 Claims, No Drawings

METHOD FOR THE DETERMINATION OF THE ENZYMATIC ACTIVITY OF CONVERTASE

This is a continuation of application Ser. No. 796,042, filed Nov. 7, 1985, now abandoned.

The present invention relates to a method for measuring the proteolytic activity of enzyme systems involved in the excision of active neurotransmitter fragments.

The exchange of information between connected neurons is established by means of chemical substances called neurotransmitters or alternatively neuromodulators. A large number of so-called peptidergic neurons are capable of producing substances of the peptide family—called neutropeptides—having multiple biological functions: in particular, these substances act as chemical messengers in the majority of physiological mechanisms which contribute to the homeostatic equilibrium of the individual.

Consequently, an excessive deficiency or accumulation of neurotransmitter can be the cause of more or less serious diseases; as an example, a deficiency of active somatostatin could be the cause of senile dementia.

Studies have shown that a neurotransmitter deficiency can in certain cases result directly from an enzyme deficiency insofar as the enzymes are directly involved in the formation of the neurotransmitters.

In fact, these biologically active neuropeptides are formed from precursors by enzymatic cleavage, this cleavage being effected at precise points on the chain of amino acids (AA) by highly specific enzyme systems, namely the convertases, which enable these neuropeptides to acquire their biofunctionality.

Under these conditions, knowledge and evaluation of the enzyme systems involved in the process in which the neuropeptides acquire biofunctionality, after the expression of the genes coding for their precursors, are prerequisites for a pharmacokinetic study of the control of their activity and for any curative or preventive treatment.

It is for this reason that the present invention relates to a method for determining the activity of convertases involved in the maturation of the neuropeptides.

In the method for measuring the enzymatic activity of a convertase:

(a) a biological sample containing the convertase is brought into contact with a labeled peptide substrate consisting of at least 10 AA, reproducing or mimicking the sequence of the precursor at the excision site; and (b) after conversion, the enzymatic activity of the sample is measured by determining the percentage of labeled conversion fragments relative to one or more standards.

This method of determination is based on showing the specificity of the convertases for a given substrate when the latter has a structure which mimics the sequence of the precursor in the region of the excision site.

This substrate must be fairly large, i.e. must preferably have about 10 AA distributed on either side of the excision site, in order to ensure a good recognition, but not so large that it cannot be easily synthesized.

This substrate can reproduce the sequence of the precursor but it can also mimic this sequence, i.e. differ slightly therefrom, if necessary, for reasons of convenience regarding synthesis or labeling, for example.

Thus, for example, labeling with radioactive iodine can be carried out more easily on tyrosine.

The excision site generally consists of a doublet of dibasic amino acids (AA), i.e. a doublet containing Arg and/or Lys, for example Arg-Lys, or their triplet or quadruplet of the same type.

Although radioactive labeling of the substrates is convenient, it is possible to envisage other types of labeling to give "cold substrates", for example fluorescence labeling or even labeling capable of giving rise to color reactions. These peptide-labeling processes are known.

The substrate itself is essentially a peptide and can be synthesized by chemical techniques known in the art, although it is possible to envisage other types of synthesis, for example biological types.

Although the substrate is preferably synthetic, the possibility of obtaining it from an extraction product is not excluded in certain cases.

The biological samples can be of a very wide variety of origins and may possibly have been treated in order to ensure a correct determination; for example, the sample involved may be cerebrospinal fluid for detecting somatostatin convertase.

The conditions under which the sample and substrate are brought together do not constitute characteristic features, will vary according to the determinations to be carried out and will depend especially on the optimum temperatures and pH for the activity of the convertase determined. The determination itself can be carried out in accordance with modalities which can easily be understood by those skilled in the art. In fact, the excision must lead to the formation of labeled fragments which can be separated by virtue of their molecular weight. By comparison with a standard labeled solution of the said fragment, this test makes it possible to measure the activity of the convertase. A prior standardization can also be carried out with known convertase activities. Other techniques can obviously be envisaged.

Different experimental cases will be studied below in order to provide a better understanding of the procedure employed.

It has been known for a long time that attack of the cortical neurons is the cause of presenile dementia in elderly people. Now, recent studies have shown that this impairment of mental activity is due to a deficiency of somatostatin 14 in the hypothalamus, which is why it is of interest to be able to determine the somatostatin convertase by the method forming the subject of the invention. In fact, the direct precursor of somato 14 is a peptide consisting of 28 AA, namely somato 28, which is itself derived from a precursor having an MW of 15,000 Dalton.

The sequence of somato 28 is as follows:

Ser—Ala—Asn—Ser—Asn—Pro—Ala—Met—Ala—Pro—Arg—Glu—Arg—Lys—

Ala—Gly—Cys—Lys—Asn—Phe—Phe—Trp—Lys—Thr—Phe—Thr—Ser—Cys
                |                                                                           |
                S————————————————————————S

It has been demonstrated that the site of activity of the somatostatin convertase is the doublet of dibasic AA: Arg-Lys; thus, after conversion, the biologically active neuropeptide released is somato 14, which has the following sequence:

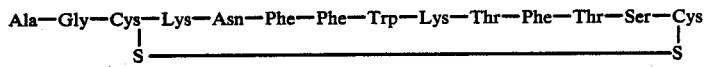

It is for this reason, taking into account the sequence of somatostatin 28, that a substrate called peptide I, having the following structure:

is used in the method of determination of the invention, M being the labeling, for example Tyr* labeled with iodine 125.

Like somatostatin 28, this peptide is converted by somatostatin convertase to give a peptide II, having the following structure:

Ala-Gly-Ala-Lys-Asn-Tyr(NH$_2$)*,　　　　　II as well as a product Asn-Tyr(NH$_2$)*, which can easily be removed by chromatography.

As stated previously, the substrate peptide may be larger, if desired, although the specificity seems to be sufficient with the proposed peptide I.

Determination of the peptide II makes it possible to measure the activity of the somatostatin convertase.

Likewise, it is possible to determine the activity of corticoliberin convertase (CRF convertase), which is active in the production of corticoliberin, a factor in the hypothalamus which is involved in the release of adrenocorticotropin by the anterior lobe of the pituitary gland.

In this way, the pharmacologist would have a means of influencing the nervous control of peripheral reactions to stress.

The substrate used in this case is synthesized with regard to the structure of the precursor CRF 41 containing 41 amino acids with a doublet Arg$^{35}$Lys$^{36}$, which is cleaved by the CRF convertase. The substrate reproduces the sequence 31→41 of the CRF:

Ala-Tyr-Ser-Asn-Arg-Lys-Leu-Leu-Asp-Ile-Ala(NH$_2$)*.

The determination is carried out as before and concerns fragments 31 to 34 and 37 to 41.

Other substrates enable the activity of ocytocin convertase, which enzyme is also known as neurophysin convertase and is referred to herein as ocytocin convertase, neurophysin convertase and ocytocin/neurophysin convertase to be determined.

This is done using the following substrates:

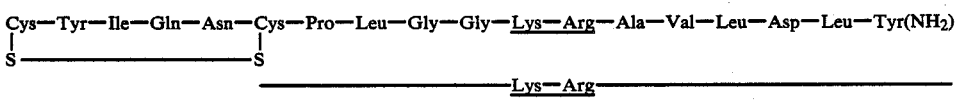

The present invention also relates to the substrates, i.e. peptides of at least 10 AA, reproducing or mimicking the structure of a neuropeptide precursor around an excision site cleaved by convertases, and in particular to the substrates described above, it being possible for the said substrates to be labeled or unlabeled.

The invention also relates to the convertases obtained, which are useful especially for carrying out the method of determination according to the invention, and in particular to somatostatin convertase.

This somatostatin convertase is a protease of about 90 kDa which cleaves somatostatin 28 to give somatostatin 14.

Further characteristics and advantages of the present invention will become apparent from the examples below.

EXAMPLE 1

Synthesis of the Substrate Peptides

The mimicking peptides were synthesized for the determination, either to be used as the substrate or to prove the specificity of the determination. The peptides I and II were synthesized by an improved version of the solid phase method using a benzhydrylamine resin (Beckman apparatus). The crude peptides were separated from the resin with liquid hydrofluoric acid at 0° C. and filtered on a Sephadex G.10 column in a 0.5M acetic acid solution. The final purification was performed by chromatography on carboxymethylcellulose. The purity of the peptides was checked by two methods:

high performance liquid chromatography using a VYDAC 201 TP column (250×4.6 mm), elution being carried out with a 5%-30% gradient of propan-2-ol in 0.1% trifluoroacetic acid solution, and analysis of the amino acids on a Beckman TSM automatic analyzer.

Labeling with iodine 125 was carried out by the lactoperoxidase method. The peptides labeled with iodine 125 were purified by ion exchange chromatography on a carboxymethylcellulose resin (CM 52). The peptide I was eluted with a buffer solution of ammonium acetate (pH 6) at a concentration varying between 150 and 300 mM. The peptide II was eluted with the same buffer solution at a concentration varying between 50 and 120 mM.

EXAMPLE 2

Preparation of Physiological Samples Containing Somatostatin Convertase Activity Male Wistar rats (100–120 g) were sacrificed by quick decapitation and the cerebral cortex was removed immediately. The fresh dissected tissue was homogenized in a Potter Elvehjem apparatus in a buffer solution of phosphate (pH 7.4) at a concentration of 50 mM and potassium chloride at a concentration of 200 mM (5 ml of buffer per cortex).

The extract was then centrifuged at 3000×g for 15 minutes and the supernatant was filtered on a Sephadex G-150 column in 0.25M Tris-HCl (pH 7). The fractions possessing proteolytic activity were then combined and subjected to ion exchange chromatography on a mono Q column (cationic) using a rapid protein liquid chromatography system (Pharmacia, Uppsala, Sweden).

EXAMPLE 3

Preparation of Purified Somatostatin Convertase

The somatostatin convertase extracted from the cerebral cortex was partially purified by molecular filtration using a Sephadex G-150 column. A specific cleaving activity was discovered, which is associated with fragments eluted as species having an approximate size of 90 KDa. The products generated by this particular enzyme fraction were characterized by determination of the terminal NH$_2$ using the double coupling method. The results showed the presence of an isolated alanine residue at the terminal NH$_2$ end of the peptide eluted on an ion exchange column with ammonium acetate at a concentration varying from 30 to 100 mM (peptide II).

Another type of proteolytic activity, with an apparent size of 46 KDa, appeared from this fractionation. The peptide I was also converted by this fraction to the peptide II, but to a much lesser extent.

In addition to this major proteolytic activity, another protease was detected in the fractions eluted as species of 60 KDa. It seems that this corresponds to an undesirable activity generating the dipeptide fragment Asn-$^{125}$I-Tyr(NH$_2$), as proved by ion exchange chromatography and analysis of the terminal NH$_2$. The 90 KDa fraction was consequently subjected to ion exchange chromatography on a cationic resin. The activity eluted between 80 and 120 mM NaCl was essentially free of the undesirable contaminating activity. Consequently, this proteolytic fraction was used as the conversion source in all the experiments described. To remain stable, this enzyme had to be stored at 4° C. Under these conditions, it actually retained its total activity for several days. The optimum pH for its specific activity was approximately 7 with a rapid decline below 6.

EXAMPLE 4

Method for Determining Somatostatin Convertase

The proteolytic activities were tested in the following way. The peptide I labeled with iodine 125 (20,000 cpm), dissolved in 10 μl of 250 mM Tris-HCl (pH 7), was incubated at 37° C. with an aliquot either of crude extract of rat cerebral cortex or of fractions derived from gel filtration or derived from ion exchange chromatography (final volume of 300 μl in 0.25M Tris-HCl (pH 7)).

50 μl samples of the mixture were taken at different times during the reaction and the reaction was stopped by the addition of 600 μl of CM-52 resin in 30 mM ammonium acetate (pH 6) (1:10, vol./vol.). The mixture was then centrifuged at 10,000×g for 30 seconds on a Beckman microcentrifuge. The resulting centrifugation residue was washed once with the same buffer and then twice with a buffer solution of ammonium acetate (pH 6) at a concentration of 100 mM. After the second washing by elution at each of its saline concentrations, the iodinated products retained on the resin were counted.

The results were calculated as follows:

$$\text{Specific activity} = \frac{(x_1 - x_2) - (y_1 - y_2)}{y_2} \times 100$$

$$\text{Undesirable activity} = \frac{(t - x_1) - (t - y_1)}{y_1} \times 100,$$

where the specific activity represents the percentage of peptides II generated, the undesirable activity represents the percentage of Asn-$^{125}$I-Tyr(NH$_2$) generated, t is the total cpm in 50 μl of the mixture, $x_1$ is the cpm found after washing with the 30 mM ammonium acetate, $x_2$ is the cpm found after washing with the 100 mM ammonium acetate, and $y_1$ and $y_2$ are the cpm values found respectively after the 30 mM and 100 mM washings of the resin with the peptide I by itself.

RESULTS

The evaluation of the specific and undesirable activities in three regions of the brain is expressed in the table which follows:

| Region of the brain | % OF PRODUCTS GENERATED | |
|---|---|---|
| | Peptide II labeled with 125$_I$ | Asn-$^{125}$I-Tyr(NH$_2$) |
| Hypothalamus | 7 | 90 |
| Neocortex | 18 | 40 |
| Pituitary gland | 20 | 37 |

The extracts were obtained from three regions of the brain and were fractionated by filtration on a molecular sieve. A 50 μl aliquot corresponding to an activity peak was incubated with the peptide I (20,000 cpm) for 2 hours and the products were analyzed by ion exchange.

The results are expressed as a percentage (%) of the starting materials and show that the hypothalamus is the center of a substantial undesirable activity, in contrast to the neocortex and pituitary gland, which seem to be more appropriate for analysis of the specific enzymatic cleavage.

EXAMPLE 5

Specifically of Somatostatin Convertase

The ability of several analogous peptides to compete with the peptide I in the enzymatic conversion was evaluated by means of competition experiments. The results given in the table which follows indicate that either the peptide of 28 AA (S-28) or the noniodinated substrate of II AA (deiodinated peptide I) competed effectively (75% and 85% respectively) with the iodinated peptide I. It is interesting to observe that simple replacement of Lys with Arg in the dibasic doublet (cleavage site) produced a peptide III, which competed with the iodinated substrate (peptide I) with an efficacy of only 30%.

Finally, no inhibiting activity was detected when using a peptide fragment of the CRF possessing a doublet Arg-Lys and a different sequence on either side of this site (peptide IV).

| EFFECT OF DIFFERENT PEPTIDES ON THE CONVERSION ACTIVITY | |
|---|---|
| COMPETING PEPTIDE | % INHIBITION |
| De—$^{125}$I—Peptide I | 85 |

| EFFECT OF DIFFERENT PEPTIDES ON THE CONVERSION ACTIVITY | |
|---|---|
| COMPETING PEPTIDE | % INHIBITION |
| Pro—Arg—Glu—<u>Arg—Lys</u>—Ala—Gly—Ala—Lys—Asn—Tyr(NH₂) | |
| Peptide III | 30 |
| Pro—Arg—Glu—<u>Arg—Arg</u>—Ala—Gly—Ala—Lys—Asn—Tyr(NH₂) | |
| Peptide IV | 0 |
| Ala—Tyr—Ser—Asn—<u>Arg—Lys</u>—Leu—Leu—Asp—Ile—Ala(NH₂) | |
| Somatostatin 28 | 75 |

The enzyme prepared from the Sephadex G-150 column was incubated in a mixture containing either 1 μl of each of the peptides described above or 2 μg of somatostatin 28 and $^{125}$I—Peptide I (30,000 cpm) in a buffer solution of Tris-HCl (pH 7) at 37° C. for 2 hours. 0% inhibition corresponds to a maximum conversion of the peptide I to the peptide II.

We claim:

1. A method for measuring the enzymatic activity of a convertase that enzymatically cleaves a neuropeptide precursor at an excision site comprising:
   (a) contacting a biological sample containing the convertase with a labeled peptide substrate consisting of at least 10 amino acids and no more than 20 amino acids, reproducing or mimicking the sequence of the precursor at the excision site,
   (b) incubating for a time to allow for conversion, and
   (c) measuring the enzymatic activity of the sample by determining the precentage of labeled conversion fragments relative to one or more standards.

2. The method as claimed in claim 1, wherein the peptide substrate is labeled with a radioactive element.

3. The method as claimed in claim 1, wherein the peptide substrate is labeled with a non-radioactive element.

4. The method as claimed in claim 1 or 2, wherein the peptide substrate is labeled with iodine 125.

5. The method as claimed in any one of claims 1, 2, 3 or 4, wherein the convertase assayed is somatostatin convertase and the peptide substrate has the formula:

Pro-Arg-Glu-Arg-Lys-Ala-Gly-Ala-Lys-Asn-Tyr(NH₂).

6. The method as claimed in any one of claims 1, 2, 3 or 4, wherein the convertase assayed is corticoliberin (CRF) convertase and the peptide substrate has the formula:

Ala-Tyr-Ser-Asn-Arg-Lys-Leu-Leu-Asp-Ile-Ala(NH₂).

7. The method as claimed in any one of claim 1, 2, 3 or 4, wherein the convertase assayed is ocytocin/neurophysin convertase and the peptide substrate has the formula:

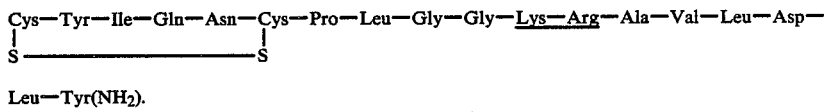

Leu—Tyr(NH₂).

* * * * *